(12) United States Patent
Wadman

(10) Patent No.: US 7,872,754 B2
(45) Date of Patent: Jan. 18, 2011

(54) OPTICAL MEASUREMENT DEVICE

(75) Inventor: Sipke Wadman, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 277 days.

(21) Appl. No.: 12/296,971

(22) PCT Filed: Apr. 10, 2007

(86) PCT No.: PCT/IB2007/051274

§ 371 (c)(1),
(2), (4) Date: Oct. 13, 2008

(87) PCT Pub. No.: WO2007/119202

PCT Pub. Date: Oct. 25, 2007

(65) Prior Publication Data

US 2009/0174878 A1 Jul. 9, 2009

(30) Foreign Application Priority Data

Apr. 18, 2006 (EP) .................................. 06112699

(51) Int. Cl.
*G01N 21/55* (2006.01)
(52) U.S. Cl. .................................................... 356/445
(58) Field of Classification Search ......... 356/445–448, 356/450–458
See application file for complete search history.

(56) References Cited

U.S. PATENT DOCUMENTS

| 4,575,252 | A | * | 3/1986 | Akiyama | 356/446 |
| 4,913,150 | A | * | 4/1990 | Cheung et al. | 600/323 |
| 5,241,369 | A | * | 8/1993 | McNeil et al. | 356/445 |
| 5,912,741 | A | * | 6/1999 | Carter et al. | 356/445 |
| 6,122,042 | A | * | 9/2000 | Wunderman et al. | 356/73 |
| 6,173,196 | B1 | * | 1/2001 | Delonzor et al. | 600/310 |
| 6,292,576 | B1 | * | 9/2001 | Brownlee | 382/124 |
| 6,490,470 | B1 | * | 12/2002 | Kruger | 600/407 |
| 6,577,397 | B1 | * | 6/2003 | Wadman | 356/446 |
| 6,630,673 | B2 | | 10/2003 | Khalil et al. | |
| 6,643,020 | B2 | | 11/2003 | Mizushima et al. | |
| 2004/0133086 | A1 | * | 7/2004 | Ciurczak et al. | 600/322 |
| 2005/0002031 | A1 | * | 1/2005 | Kraemer et al. | 356/337 |

(Continued)

FOREIGN PATENT DOCUMENTS

EP 0864856 A1 9/1998

(Continued)

*Primary Examiner*—Gregory J Toatley
*Assistant Examiner*—Jarreas C Underwood

(57) ABSTRACT

An optical measurement device for measuring an optical appearance of a surface of a sample, in particular the surface of a human skin, wherein the optical measurement device comprises: a first illumination device (16) for illuminating the surface (14) with a first illumination beam (22), wherein the first illumination beam (22) is incident at a first angle of incidence (38) onto the surface (14); and a detection device (28) for detecting a response beam (22), wherein the response beam (42) is a response of the sample (12) to the first illumination beam (22), comprising at least one screen (27) for intercepting the response beam (42) and at least an image detection component (29). The optical measurement device (10) comprises a second illumination device (18), wherein the second illumination device (18) is providing a second illumination beam (24) with a second angle of incidence (54) at the surface (14), wherein the first angle of incidence (38) is different from the second angle of incidence (54).

20 Claims, 7 Drawing Sheets

U.S. PATENT DOCUMENTS

2006/0092418 A1   5/2006   Xu et al.

FOREIGN PATENT DOCUMENTS

| WO | 2000037923 | A1 | 6/2000 |
| WO | 2001095800 | A2 | 12/2001 |
| WO | 2002069792 | A1 | 9/2002 |
| WO | 2004038388 | A1 | 5/2004 |
| WO | 2004077032 | A1 | 9/2004 |
| WO | 2004077033 | A1 | 9/2004 |

* cited by examiner

OPTICAL MEASUREMENT DEVICE

The invention relates to an optical measurement device for measuring an optical appearance of a surface of a sample, in particular the surface of a human skin, wherein the optical measurement device comprises a first illumination device for illuminating the surface with a first illumination beam, wherein the first illumination beam is incident at a first angle of incidence onto the surface, and a detection device for detecting a response beam, wherein the response beam is a response of the sample to the first illumination beam, comprising at least one screen for intercepting the response beam, and at least an image detection component.

The invention relates further to a method for inspecting a surface of a sample and measuring an optical appearance of the sample, in particular the surface of a human skin, comprising the following steps: illuminating the surface of the sample with a first illumination beam incident at a first angle of incident at the surface, intercepting a response beam, wherein the response beam is a response of the sample to the at least first illumination beam.

Optical measurement devices for inspecting the surface of an object, called sample in the following, are generally known. These are calorimeters, gloss-meters, scatterometers and/or photogoniometers, used to investigate the surface of the sample.

Such an optical measurement device for measuring the optical appearance of the surface of the sample is known from the U.S. Pat. No. 6,630,673 B2.

The optical measurement device comprises in general a means for illuminating the surface, called illumination device in the following, and a means for detecting a radiation beam after the interaction of the illumination beam with the surface of the sample, called response beam. Herein, generally spoken, the illumination beam is reflected and/or scattered and/or absorbed at the surface of the sample to be inspected in order to generate the response beam. The generation of fluorescence light can as well be introduced by the illumination beam.

The different optical measurement devices, mentioned above, are sensitive for different optical appearances of the surface of the sample. The calorimeter is sensitive for different colors of the surface, the scatterometer is sensitive for the radiation beam scattered at the surface and so on.

The surface having the optical appearance can be described by different parameters or properties. These are mechanical properties like roughness, texture, hardness, friction resistance, and so on. The properties assigned to the visual appearance are: being glossy, shiny, dull and having a consistant color or consisting of color flops and so on.

The properties of the surface causes different interaction patterns with the illumination beam, like different degrees of reflection, different absorption coefficients, different scattering behaviour and/or transmission in case of a translucent or transmissive surface.

In most of the optical measurement devices one of the above-mentioned properties are measured and a correlation between, for example, the roughness and the degree of glossiness are performed using standards for comparison and a data base or an assigning table.

An optical measurement device, called scatterometer, is known from the U.S. Pat. No. 6,577,397 B1. The scatterometer comprises an illumination device for providing an illumination beam, illuminating a surface of a sample and a screen for intercepting radiation scattered from the sample location and a radiation-sensitive detection system for capturing a two-dimensional image of the screen and converting it into an electric detector signal. The screen can be used in reflection or transmission and has the usual property of a projection screen. The two-dimensional image formed on the screen represents the angle and distribution of the radiation scattered by the sample arranged at the sample location. This instrument is also known as Parousiameter and characterizes the textures, gloss and flip-flop color effects as a quality of the optical appearance of decorated or finished products.

Human skin is a sample of great interest in the health industry, for cosmetic product development and treatment methods as well as in the field of medicine. The optical appearance of the human skin is influenced by the surface itself as well as by the sub-surface area, because the human skin is a translucent material.

The optical appearance of the human skin is completely obvious to a human observer in a subjective qualitative way. However, obtaining an objective and numerical value for the optical appearance is quite difficult, because the skin is a living surface that can change during the performed measurement. On the other hand, the human skin varies between different persons and it is therefore a challenge to find a standard decisive to find an objective way to describe the human skin in order to classify the human skin.

Therefore, there is a great demand for an objective way of a quantitative characterization of the optical appearance of the translucent human skin in the industry producing cosmetics products, medical products and so on.

From the U.S. Pat. No. 6,630,673 B2, an apparatus and method for non-invasively measurement of at least one optical parameter of a sample, particularly a sample of tissue, that comprises a plurality of layers, is known. The at least one parameter can be used to determine the presence or concentration of an analyte of interest in the sample of tissue.

The apparatus and method measure light that is substantially reflected, scattered, absorbed or emitted from a shallower layer of the sample of tissue, measure the light that is substantially reflected, scattered, absorbed, or emitted from a deeper layer of the sample of tissue and determine at least one optical parameter for each of these layers, and account for the effect of the shallower layer on the least one optical parameter of the deeper layer.

Specifying the sample depth, allows the determination of the optical properties of a specific layer of the sample of the tissue, i.e. dermis, and decreases interferences from other layers, i.e. stratum corneum and epidermis, in these determinations.

With the device disclosed, it is possible to measure the quantity of light re-emitted from the sample, in particular the arm of a human patient and estimate from a comparison different absorption coefficients of the skin.

It is not possible to determine the overall optical appearance of the skin using the above-mentioned optical measurement device.

Therefore, it is an object of the present invention to provide an optical measurement device in order to estimate an optical appearance of a surface of a sample, in particular of the optical appearance of a human skin.

The object is solved according to the present invention with an optical measurement device according to the one mentioned at the outset, in that the measurement device comprises at least a second illumination device, wherein the second illuminating device provides a second illumination beam with a second angle of incidence at the surface, wherein the first angle of incidence is different from the second angle of incidence.

The use of a first illumination device and a second illumination device is advantageous, because the sample can be illuminated with different illumination parameters, like intensity of the illumination beam, wavelength and/or angle of incidence of the illumination beam, resulting in a different response beam. For example, the penetration depth into the surface of the sample is dependent on the wavelength and the angle of incidence of the illumination beam.

Due to the different penetration depths of the two illumination beams, the illumination of the surface of the sample with the two different illumination beams, having different angles of incidence, gives access to the surface and the sub-surface areas of the sample, wherein the sub-surface areas are different.

The response beam, generated at the surface and in the sub-surface areas is measured with a detection device, wherein the detection device comprises at least one screen and a radiation-sensitive image detection component. Herein the response beam is intercepted by the screen and the two-dimensional image of the screen is captured by the radiation-sensitive detection component and converted into an electric detector signal. The two-dimensional image, formed on the screen, represent the angular distribution of the response beam that is a response of the sample to the illumination with the first illumination beam and/or the second illumination beam. The image is therefore a Fourier-like transform of the physical properties of the sample, in which a special variation and physical properties of the sample is transformed to an angular variation of radiation energy.

Depending on the first illumination beam and the second illumination beam, the Near field and/or the Far field and/or the Deep field can be detected. The Near field describes the image of the surface—what is visible to an observing eye—taken with the radiation-sensitive image detection component.

The Far field describes how a surface reflects the illumination beam in the distance in angular terms of diffuse scattering, glossy reflections, viewing angle affects and so on. While the result of the Far field effects are visible, like gloss, the Far field distribution itself is invisible. The Far field is captured with the screen forming a two-dimensional image on the screen, wherein the two-dimensional image on the screen is captured by the radiation-sensitive image detection component.

The Deep field describes how an illumination beam is re-emitted from a translucent material, wherein the response beam is the response from the sub-surface area scattering the illumination beam and re-emitting the response beam from the surface at a location away from an entry point of the illumination beam. Therefore, to measure the Deep field, the illumination of a surface with a illumination spot is necessary to obtain the Deep field.

Depending on the illumination beams, which are characterized by the angles of incidence, the Near field, the Far field and/or the Deep field can be detected.

With that, at least two different parameters, added up to the optical appearance of the surface of the sample, are accessible with the optical device according to the invention.

The response beam can be formed by reflection and/or scattering including scattering from different areas at the surface itself and/or in sub-surface areas. Access to properties of the surface layers and the sub-surface areas in different depth is given and the properties can be estimated.

In a first preferred embodiment of the invention, the optical measurement device comprises a third illumination device, providing a third illumination beam with a third angle of incidence at the surface, wherein the third angle of incidence is different from the first and/or the second angle of incidence.

The first illumination device, the second illumination device and the third illumination device comprises in particular semiconductor lasers LEDs and/or a tungsten halogen radiation sources emitting a first radiation beam, a second radiation beam and/or a third radiation beam, wherein the radiation beams have different wavelengths or the same wavelength, but according to the invention different angle of incidence at the surface of the sample.

The intensities of the at least three radiation beams can be similar or different. With that, the sub-surface area of a skin, being a translucent material, can be inspected as well as the surface of the human skin.

The first and/or second and/or third illumination device can be arranged at different locations in the optical measurement device, in order to realize the different angles of incidence of the illumination beams at the surface.

In a further preferred embodiment of the invention, the image detection component is a camera, in particular a digital camera.

The use of a camera as the image detection component, allows a fast capture of an image, wherein the image is the full distribution of the scattered illumination beam at the surface or in the sub-surface area. The camera can be a video camera, a normal analogue camera as well as a digital camera, in particular a camera with CCD or CMOS-detector. The use of a digital camera has the advantage that the output of the digital camera is already providing a data file with the full information of the image.

In a further preferred embodiment, the screen is a full hemispherical screen, intercepting the response beam in about 360° in azimuth, 180° in inclination above the surface of the sample, resulting in a wide field.

A screen is a simple and cheap way for intercepting the response radiation. The screen is in particular coated with a coating in order to perform the visualization of the intercepted response.

A full hemispherical screen is advantageously used to intercept a great quantity of the response beam. The two-dimensional image describes the Far field, being the response of the surface in the distance in angular terms of diffuse scattering, glossy reflections, viewing Angle Effects. The result is a pattern of a light distribution. With that, the effect of the Far field distribution, for instance scatter centers, glossy reflection centers and so on, are visible. Due to the large angle of 360° above the surface of the sample the total amount of the light reflected and/or scattered from the surface is intercepted by the screen, resulting in a good sensitivity.

In a further preferred embodiment, the screen is a substantially flat screen, covering approximately a quarter hemisphere.

The screen covering approximately a quarter hemisphere needs only little space. The arrangement of the screen is advantageously such that a device performing the illumination of the surface and the angle for the interception of the response beam on the screen is about 90°. The space gained by using the above discussed screen can be used in order to arrange the illumination device close to the surface.

Such an optical measurement device can be used for inspecting surfaces having concave curved surfaces and/or using the optical measurement device with a mobile measuring head inspecting surfaces of bigger objects or at hidden parts with very little space.

In a further preferred embodiment, the optical measurement device comprises a base plate, having a measuring port through which the both illumination beam in order to illuminate the surface and the response beam towards the detection device are propagating.

Using a measuring port allows the separation of the illumination beam and the response beam, detected in the detection device.

The use of the measuring port allows to choose a specific area of the total surface of the sample and to illuminate a selected area.

In a further preferred embodiment, the measuring port is designed such that a small area of the surface of the sample is covered, in order to achieve a good spatial resolution.

A measuring port in the optical measurement device that is designed such that a small area of the surface to be inspected is covered has the advantage, that small areas of the surface can be illuminated with the illumination beam, wherein the illumination beam is propagating through the measuring port.

The use of a small measuring port has additionally the advantage that the base plate can be designed of a very small shape. The base plate is the part of the optical measurement device, which is in contact with the surface of the sample. A small base plate having a small measuring port allows realizing a small contact area of the optical measuring device. With that surfaces which are curved, in particular negatively curved surfaces can be investigated, wherein the base plate is brought into contact with the concave surface.

In the further preferred embodiment of the invention, the measuring port has the shape of an elongated aperture in order to detect the response beam that is the response of the sample to the illumination beam scattered at a sub-surface area, wherein the response beam is generated in a distance from the location of the illumination beam incident on the surface.

Due to the fact that the response beam, which is the response of the sample to the illumination beam scattered at a sub-surface area is generated in a distance from the location of the illumination beam incident on the surface, the use of a rectangular measuring port would cut off the deep scattered illumination beam, wherein the wording deep scattered is used for the scattered illumination beam at a sub-surface area. The use of an elongated aperture allows the detection of the deep scattered illumination beam.

According to a further preferred embodiment of the invention, the illumination beam at the surface is directly reflected cut off by means of a substantially vertical baffle arranged in the elongated aperture.

Preferably the elongated aperture is divided in an illumination part and a detection part by the baffle.

The direct reflected illumination beam at the surface of the sample is of a higher intensity than the illumination being scattered in the sub-surface area. Therefore, in order to obtain a good intensity resolution in the detection device, it is advantageous to detect only the scattered illumination beam.

Further, this allows a separation of the illumination beam and the response radiation beam in order to shield the illumination beam, which is in general a very intensive radiation beam.

According to a further preferred embodiment of the invention, the elongated aperture is designed such that the response beam shows a spatial distribution related to a depth at which the illumination beam was scattered in the sub-surface area.

Due to the longish shape of the elongated aperture, the response beam is able to pass the elongated aperture, wherein the response beam comprises a spatial distribution which is related to the depth, in which the illumination beam is scattered. The illumination beam is incident at a so-called illumination spot, which is the point of incidence at the surface of the sample. The illumination beam is penetrating in a sub-surface area, wherein the sub-surface area extends to a certain depth. The illumination beam is scattered at the surface, in a first depth of the sub-surface area, in a second depth of the sub-surface area, and so on. Depending on the depth, the illumination beam is scattered, the scattered illumination beam is re-emitted from the surface at different locations from the illumination spot, forming the response beam with the spatial distribution. Herein, the scattered illumination beam in a lower depth is re-emitted at a location closer to the illumination beam scattered at a deeper depth.

With that, the Deep field is accessible, because the response radiation beam comprises the illumination beam scattered at the surface and in different depths of the sub-surface areas of the surface of the sample in case the surface comprises a translucent material. The illumination beam scattered in the sub-surface area is re-emitted from the surface at a location away from the illumination spot.

In a further preferred embodiment, the optical measurement device comprises components for separating the response beam from the illumination beam.

These are in general so-called shielding baffles, arranged in the optical measurement device at positions selected depending on the measurement to be performed. They are necessary because the illumination spot on the surface is relatively bright and causes overexposure of the detection device, in particular if the detection device is a camera.

According to a further preferred embodiment of the invention, the optical measurement device comprises at least one mirror for imaging the response beam intercepted by the screen into the image detection component.

The use of at least one mirror in the optical measurement device allows the positioning of the image detection component in different positions. In case the response beam is directly imaged by the image detection component, the imaged detection component has to be positioned in a direct optical path of the response beam in order to detect the response beam. Depending on the design of the optical measurement device it can be advantageous to position the image detection component for instance at an angle of between 30° and 80° with respect to the surface of the sample, from which the response beam is emitted.

This is due to the fact that, for instance illumination devices and other optical components have to be positioned necessary in the direct optical path of the response beam which is substantially perpendicular to the surface of the sample. The mirror can also act as shielding baffle.

In a further preferred embodiment of the invention, each of the first illumination device and/or the second and/or the third illumination device comprises a first and/or a second and/or a third radiation source and/or a first and/or a second and/or a third fiber for directing the first and/or second and/or third illumination beam onto the surface of the sample.

With that, different designs of the optical measurement device are possible.

A first embodiment of the optical measurement device comprising a first radiation source which is connected with a first fiber a second radiation source which is connected with a second fiber and a third radiation source which is connected to a third fiber is also possible. Herein the first radiation source can emit a radiation beam with a first wavelength, the second radiation source can emit a radiation beam with a second wavelength and a third radiation source can emit a third radiation beam with a third wavelength. The radiation beam can be directly be incident as illumination beam on the surface of the sample or can be directed by means of fibers to the surface of the sample. With that the optical measurement device has a great flexibility concerning the variety of illumination beams with different properties like wavelength, angle of incidence and other properties like illumination spot size, which is the size of the illumination beam at the illumination point.

In a further preferred embodiment, the optical measurement device comprises a first radiation source and a first, a second and a third fiber, wherein the first fiber realizes the first angle of incidence, the second fiber realizes the second angle of incidence and the third fiber realizes the third angle of incidence of the respective illumination beam.

This is a cost-saving solution where only one radiation source is included in the optical measurement device. This saves also space. Advantageously, the radiation source is the Xenon flash of the camera used as radiation-sensitive image detection component.

According to a further preferred embodiment, the first fiber and/or the second fiber and/or the third fiber are arrangeable in a close distance to the surface, in order to realize a small illumination spot at the surface.

This is advantageous and results in a possible great spatial resolution of the obtained image, because it is possible to position in a certain area of the surface a greater number of illumination spots in order to scan small areas segments of the surface.

According to a further preferred embodiment, the detection device comprises at least one color filter.

The scattering process in the sub-surface area causes, depending on the depth the scattering takes place, a shift of the wavelength of the re-emitted beam with respect to the illumination beam.

The use of a color filter allows a visualization of the color of the response beam. Different colors are due to different wavelengths of the response beam. The range of the colors blue to yellow are covering a wavelength domain between about 350-700 nm, wherein each color of specific wavelength is allocatable. The red color has a wavelength of approximately 633 nm for example.

According to a further preferred embodiment of the invention, the optical measuring device comprises at least one polarisation filter.

The use of at least one polarisation filter allows to analyze the polarisation state of the response beam. This is important, because a scattering and/or reflection of the illumination beam can cause a change of the polarisation plane in the response beam. Preferably a second polarisation filter is included.

According to a further preferred embodiment of the invention, the optical measurement device comprises a calculation device for determining a correlation factor out of the detected response beam.

A correlation factor, also called merit factor or factor of merit, gives a correlation between a measured value and an assigned property. With that, a correlation of the measured response beam mirrors the optical appearance, known to the user of the optical measurement device like glossy, very glossy, dull, dark, light, shiny and so on, can be performed.

The correlation factor allows to classify the information comprised in the detected response beam. In particular, the calculated values taken from the response beam are correlated to the above-mentioned classifications of the optical appearance. With that, by detecting the response beam, the output of the optical measurement device is typically like: the surface is very shiny or the surface is dull or the surface has a degree of gloss with the level 3 wherein the level has a range between 1 and 10.

The object is also solved by a method for inspecting a surface of a sample and measuring an optical appearance of the sample, in particular the surface of a human skin according to the method mentioned at the outset in that the surface is illuminated with a second illumination beam incident at a second angle of incidence at the surface, a first and/or at least a second correlation factor is estimated from the intercepted response beam and the first, and the at least second correlation factor is assigned to a first and/or second feature of the optical appearance of the sample.

The illumination beam has at least two different angle of incidences at the surface, allows to have access to depth and/or different properties at the surface and/or in sub-surface areas of the skin. The estimation of a first and/or at least a second correlation factor from the intercepted response beam and the assigning of the first and the at least second correlation factor to a first or and/or a second feature of the optical appearance allows that the user, using the optical measurement device, obtains a description and classification of the optical appearance, he or she is used to.

The estimation of the correlation factor allows additionally to condense and simplify the information that is comprised in the response beam for the custom user. It is also possible to use different data bases with different assignments according to the dedicated user.

For instance, if a scientist is using the optical measurement device, an output can be the characterization of a surface in terms of number of scatter centers or scatter ratio. If the user is a medical specialist, the output could be in terms of skin disease, like number of black centers, known for as mellanoms and so on. If the user is a specialist which uses the optical measurement device in the field of cosmetic treatments, the output could be a number of wrinkles or depth of wrinkles, before and after cosmetic treatment.

In a first aspect of a method, a second step of illuminating the surface with at least a third illumination beam and estimating at least a third correlation factor in order to obtain a third feature of the optical appearance of the sample is performed.

The use of at least three illumination beams, wherein the three illumination beams have different angles of incidence at the surface, results in a variety of obtainable informations.

According to a further aspect of the method, a data base is used in order to perform an assignment of the respective correlation factor to the respective feature of the sample.

A data base is a standard tool used in data processing. A large variety of different features and measured values, estimated from the detected response beams can be easily stored. The data base is flexible in that new data and new features can be added very easily.

It is preferably possible to choose the position and/or the angle of the first illumination beam and/or the second illumination beam and/or the third illumination beam in order to use included components like mirrors in the optical measurement device acting as shielding means.

According to a further preferred aspect of the method, the optical measurement device comprises calculation means for a calculation of an estimation of the correlation factor from the detected response radiation beam.

With a correlation factor, the reflection and/or scattered pattern of the surface, carrying the information of the optical appearance of the surface can be transferred into practical terms to the user. The correlation factor is in general a possibility to condensate the overall information and extract the information of interest from the whole set of detected data. For instance, parameters known to the user like suntan, beauty, check of moles, gloss or number of dark spots, and so on can be obtained.

The estimation of correlation factors is advantageously performed using a separate measuring series using standardized surfaces to configure the data base. Herein it is important and essential for the present invention that the optical measurement device is depending on what light does with the illumination of the surface of the sample. Although reflected and/or scattered light from the surface and/or the sub-surface areas are intercepted from the integrated overall response beam, parameters, at least one parameter is evaluated that is corresponding to the special effect of interest. This is for instance the degree of glossiness, the color, the kind or degree of translucency and so on.

This is advantageous compared to different approaches, measuring obvious by single parameter with a single measurement. Using the method of the optical measurement device, the overall effect is measured and only single information are extracted from the overall effects. Herein it is not important to know what optical processes caused the extracted effects.

Due to the fact that the effects of interest can take place in three different special domains that relate to fundamentally different visual approaches, the optical method is able to measure the three special domains listed below: The Near field, the Far field, and the Deep field.

With that, the overall measured aspects of the optical appearance of the surface of a sample is transferred to the features of optical appearance known by the users and applicants of the method. A data base is storable in a storage medium like a CD, DVD or any other storage media. It is important that the data base is stored in electronic form and that the determination of the correlation factor is performed using an intelligent software from the response beam detected and transduced into electronic form by a computer.

The foregoing and further and more specific objects and advantages of the present invention will become readily apparent for those skilled in the art following detailed description of the preferred embodiment thereof, taken in conjunction with the drawings, in which.

Figure 1:
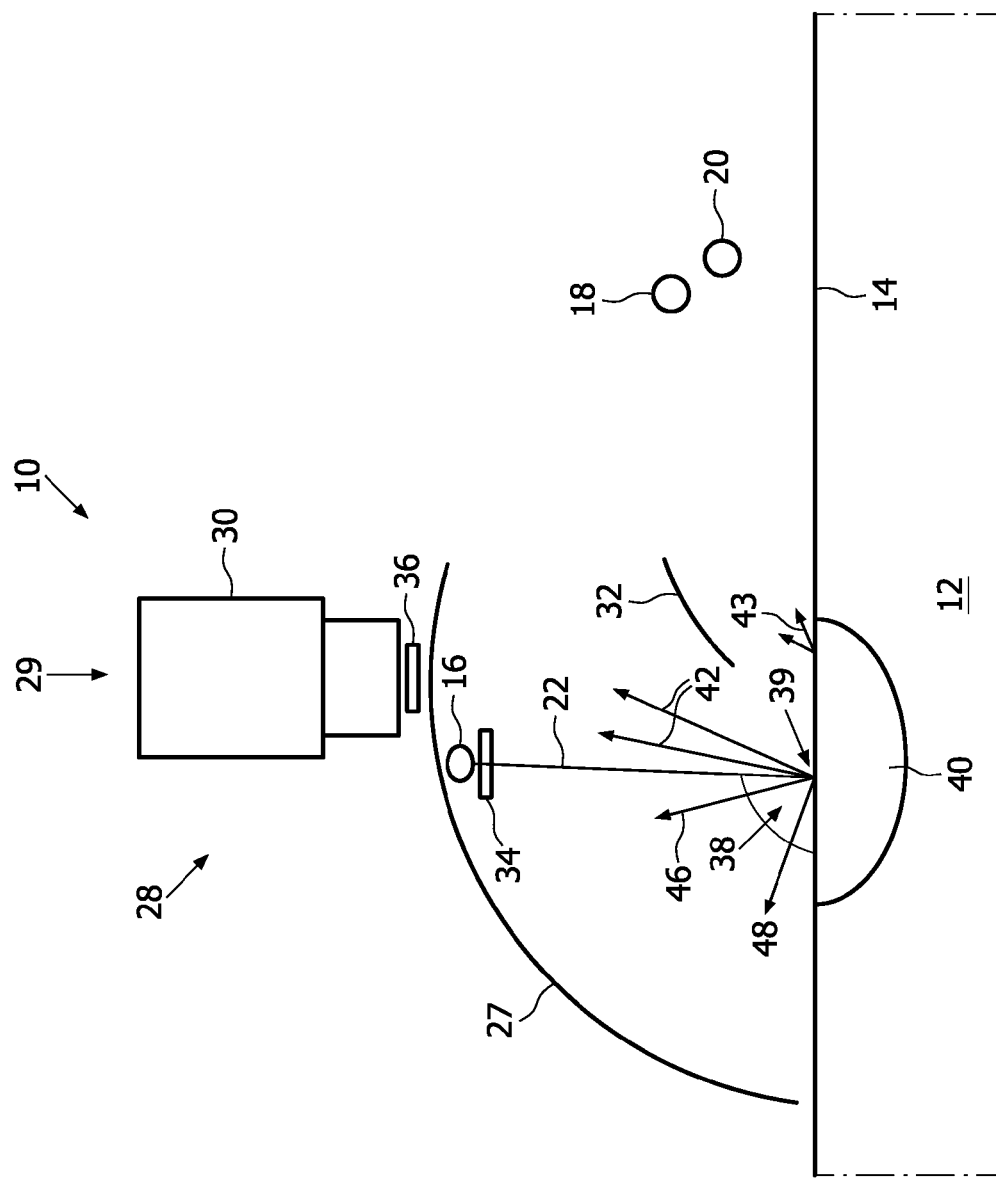
FIG. 1 shows a schematic view of a first embodiment of an optical measurement device according to the present invention.

In FIG. 1 a schematic view of an optical measurement device 10 is shown. The optical measurement device 10 is arranged on top of a sample 12, having a surface 14 to be inspected. The optical measurement device 10 comprises a first illumination device 16, a second illumination device 18, and a third illumination device 20 providing a first, a second and/or a third illumination beam 22, 24, and 26. The first 16, the second 18 and/or the third illumination device 20 may comprise a laser semiconductor laser, an LED, a Xe flash or a tungsten halogen radiation source. The optical measurement device 10 further comprises a detection device 28 comprising a screen 27 and an image detection component 29. The screen 27 shown in FIG. 1 is a hemispherical screen covering an angle of 360° in azimuth, 180° in inclination above the surface 14 of the sample 12, resulting in a wide field. It is also possible that the screen 27 is designed as a flat screen covering substantially a quarter hemisphere.

A mirror 32 as well as a first polarization means 34 and a second polarization means 36 are comprised. The first and the second polarization means are preferably arranged such that they are arranged parallel to the surface 14 of the sample 12 to be investigated.

In the following the working principle of the optical measurement means 10 is shortly described. A first illumination beam 22, provided from the first illumination device 16, is directed onto the surface 14 of the sample 12. The first illumination beam 22, emitted from the first illumination device 16 has a first angle of incidence 38 at the surface 14 of the sample 12. The first illumination beam 22 interacts with the surface 14 and is penetrating into a sub-surface area 40 of the sample 12 in case of a translucent sample.

The location, where the illumination beam 22 hits the surface 14 is called illumination point or illumination spot 39.

Due to the property of the surface 14 and/or the sub-surface area 40, the interaction of the first illumination beam 22 results in a response beam 42 re-emitted from the surface 14 of the sample 12.

In FIG. 1, the response beam 42 is indicated by arrows, in order to indicate that the response beam 42 can have different directions with respect to the surface 14 of the sample. In principle the spatial distribution of the response beam 42 follows a cosine-distribution at each location the response beam 42 is re-emitting the surface 14 and the highest amount of the intensity is directed in forward direction, substantially perpendicular to the surface 14 of the sample 12.

In case the illumination beam 22 is scattered in the sub-surface area 40 of the sample 12, the response beam is re-emitted from the surface 14 at a location different from the illumination spot 39 indicated with arrows 43. The response beam 42 is detectable either by the screen 27 or directly by the camera 29. Herein the camera can comprise a CCD- or CMOS-detector.

In case the response beam is detected by the image detection component 29, the illumination beam 22 passes the first polarization means 34 and the response beam passes the second polarization means 36, wherein the first polarization means 34 and the second polarization means 36 performs the distinguishing between the first part 46 and the second part 48 of the response beam 42.

Herein the first part 46 is the directly reflected illumination beam 22 at the surface and the second part 48 is the illumination beam 22 scattered at the surface or in the sub-surface area 40. For convenience in the following the first part 46 is called reflected response radiation beam 46 and the second part 48 is called scattered response beam 48.

The distinguishing can be performed in order to the fact that a reflected response beam 46 has a different polarization than a scattered response beam 48, because every interaction process with material of the sample 12 of the surface layer 14 or the sub-surface area 40 causes a charge in the polarization.

In general, the response beam 42 including the reflected response beam 46 and the scattered response beam 48 is intercepted by the screen 27 of the detection device 28, which is in particular a hemispherical screen comprising a special coating for a visualization of the response beam 42 forming a two-dimensional image. The two-dimensional image can be imaged by the image detection component 29, which is preferably a camera 30, in particular a digital camera and/or a camera with a CCD- and/or CMOS-detector.

Herein, the response beam 42, intercepted from the screen 27, is the response beam 42, being an image of the diffuse scattering, glossy reflections, and is viewing angle effects of the scattered illumination beam 22.

Because the interaction with the surface 14 of the sample 12, depends on the properties and the composition of the sample 12 at the surface 14 and in case a surface 14 is a translucent material of the sub-surface area, the two-dimensional image is a response of the sample 12 to the illumination beam 22, indicating what the sample "does with light".

The effects of reflection and scattering takes place in at least three different special domains that are related to fundamentally different optical approaches. These special domains are called Near field, Far field and in the case of the translucent material of the surface 14 of the sample 12 below the surface called Deep field.

The Near field describes the actual surface 14 itself in special terms of homogeneity, color smoothness, spots or scratches. The Near field is captured by the image detection component 29. The result is an image, in particular a digital image, of the surface as equivalent with "what meets the eye in the first place".

The image obtained at the screen 27 of the second detection device 29 is called Far Field and describes how the surface 14 scatters the illumination beam 22, 24, 26 in the distance in angular terms of diffuse scattering, close the illumination spot 39 showing reflection, viewing angle effects and so on.

While the effects of the Far field are visible, like gloss for example, the Far field distribution itself is invisible. The Far field is captured by the screen 27 and imaged by the image detection component 29 which is in particular, the camera 30. It can be a digital camera or a video camera or a CCD camera.

The response beam 42 is, by using the camera 30, stored as a data file on a storage medium and can be further processed in a computer, not shown in FIG. 1. Using an intelligent computer program allows the estimation of a correlation factor, called figure of merit, which performs the assignment between the information obtained from the response beam 42 and the features describing the optical appearance like being glossy, shiny, dull and so on.

Figure 2:
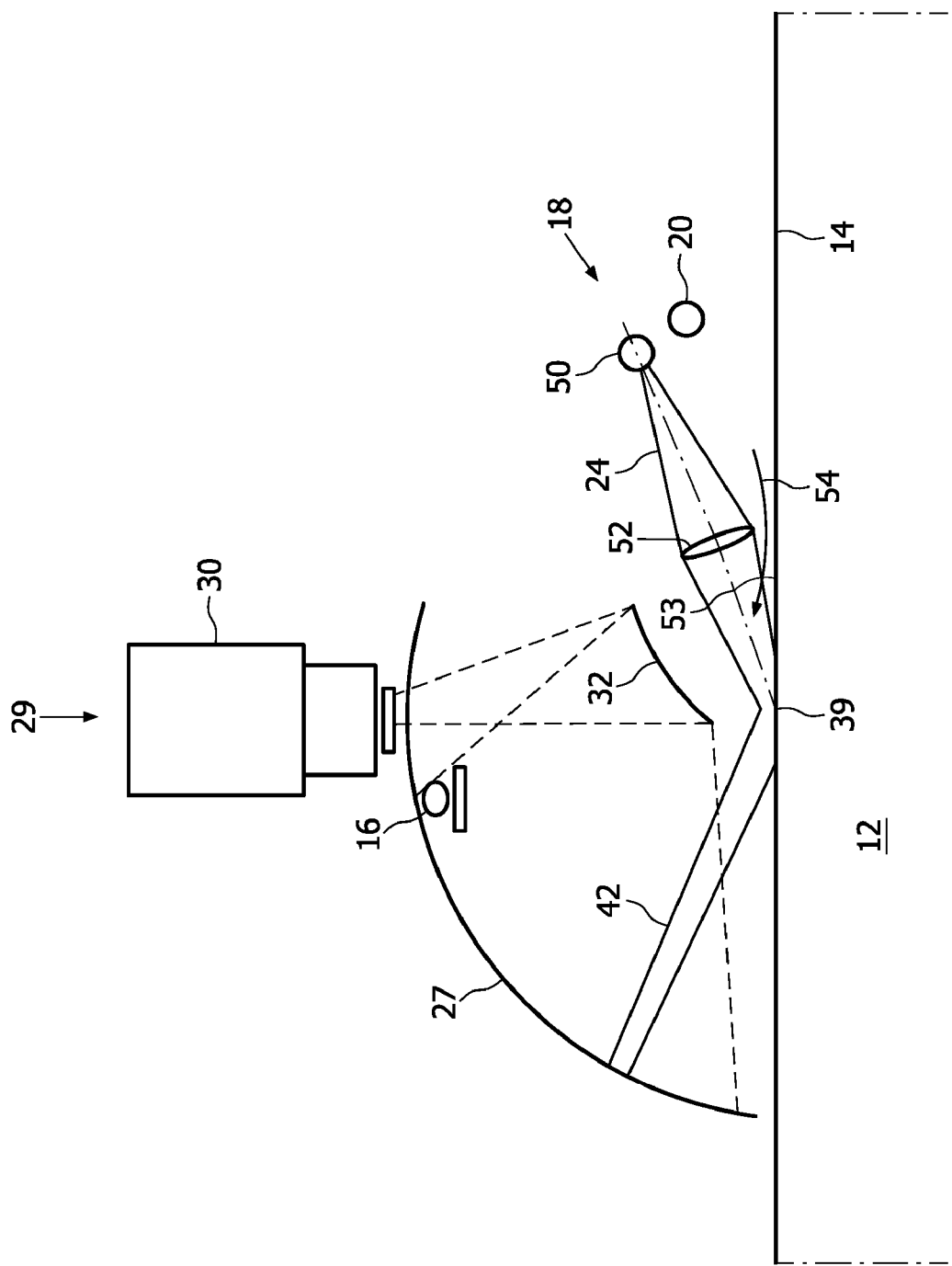
FIG. 2 shows a schematic view of the optical measurement device using a second illumination device.

In FIG. 2 the optical measurement device 10 depicted in FIG. 1 is shown, wherein the used second illumination device 18 is irradiating the surface 14 of the sample 12 performing the Far field measurement.

Same parts are assigned with same reference numbers as in FIG. 1.

The illumination device 18 comprises a radiation source 50 and a lens 52 in order to direct a collimated illumination beam 22, onto the surface 14.

The radiation source 50 can be a semiconductor laser, an LED, a XE flash or a tungsten halogen lamp.

The illumination device 18 has an optical axis 53, wherein the optical axis 53 defines an angle 54, which is assigned as a second angle of incidence 54 at the surface 14 of the sample. The optical axis is defined by the radiation source 50 and the lens 52.

The illumination radiation beam 24 is incident at a second angle of incidence 54 at the surface 14. After interaction with the material of the surface 14, the response radiation beam 32 is intercepted by the screen 27. Due to the fact that the illumination spot 39 is relatively bright, the direct illumination spot 39 is shielded by the mirror 32 from the opening of the camera 30 being positioned perpendicular to the surface 14.

On the other hand, if the reflection of the diffusion pattern on the screen 27 has to be imaged by the camera 30, the reflective side of the mirror means 32 is mirroring the two-dimensional image of the screen 27 into the opening of the camera 30. With that, the diffusion pattern comprising the reflected and scattered response beam 32 onto the screen 37 is imaged by the camera 30. The mirroring is indicated by the dotted lines in FIG. 2.

The screen 27 can be configured as full hemispherical screen covering the full angle of 360° in azimuth, 180° inclination above the surface 14 or as flat screen, not shown in FIG. 2. An example of a diffuse reflection in the full hemisphere, showing an unisotropic gloss reflection can be seen in FIG. 3.

Figure 3:
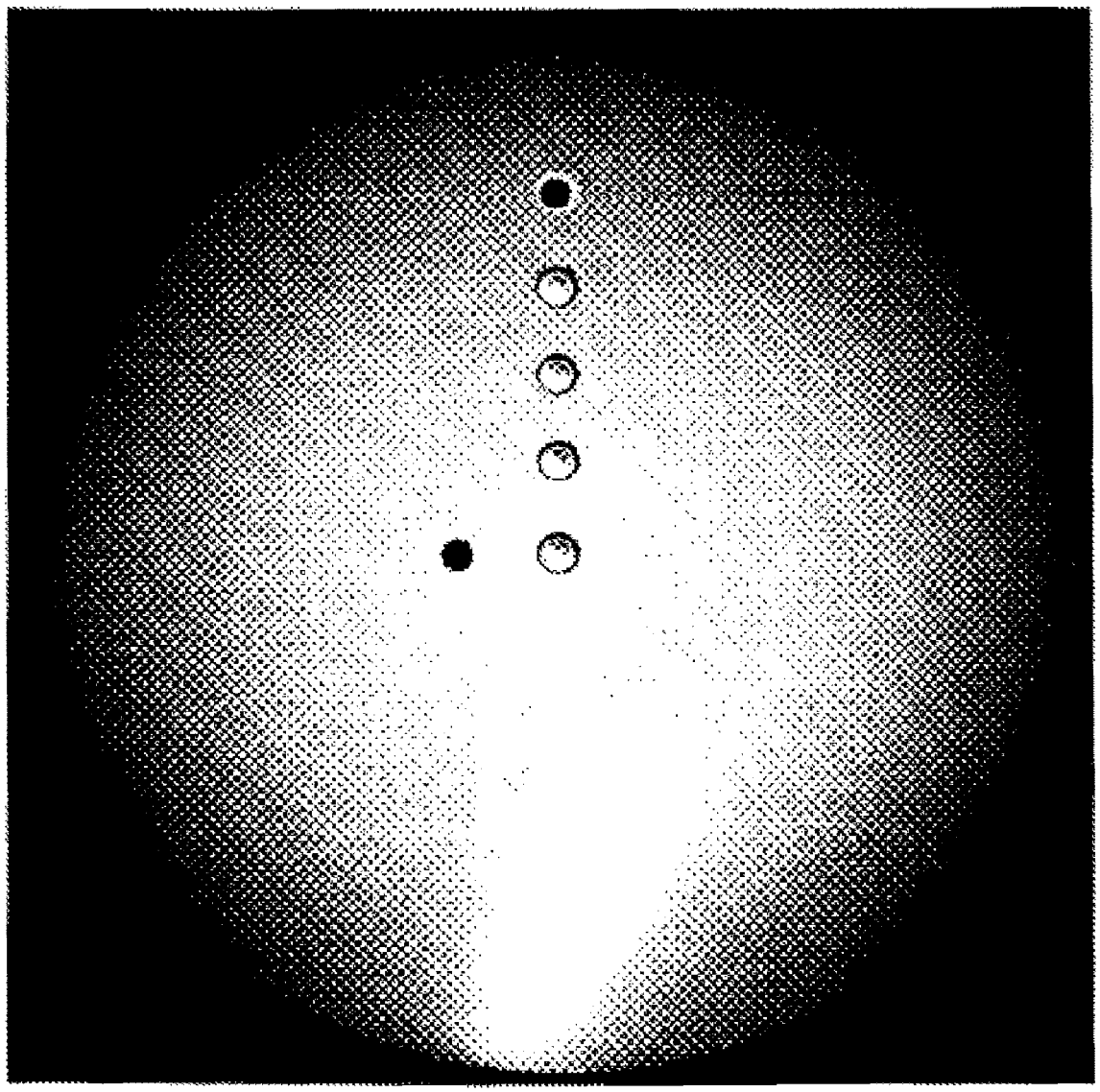
FIG. 3 shows an image of a response beam.

FIG. 3 shows a grey level diagram, called Parousiagram, taken from the image, wherein the different grey levels indicate the different intensity, which are assigned to different scatter angles.

The Parousiagram is shown as grey level diagram for the printing purpose only. This is due to the fact that a process of rastering is performed in order to obtain the grey level diagram, which is very coarse. The rastering is not a part of the measurement.

Figure 4:
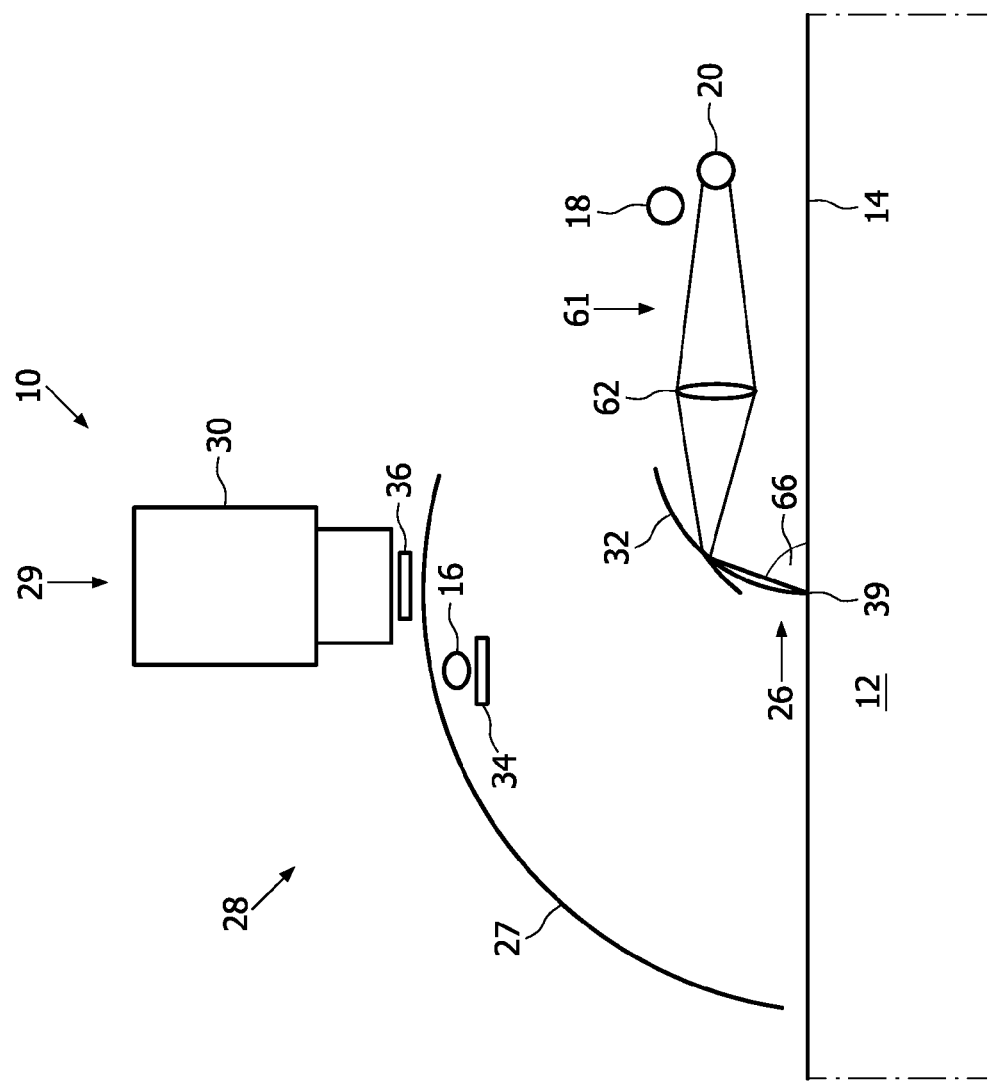
FIG. 4 shows a schematic view of the optical measurement device using a third illumination device.

FIG. 4 shows the optical measurement device 10, wherein the third illumination device 20 is used to illuminate the surface 14 to be investigated.

Herein, a radiation beam 61 emitted from a radiation source 60 from the illumination device 20 is incident on the mirror means 32, wherein the radiation beam 61 is focused by a lens 62. It is also possible to use a differently designed illumination device 20, for example a radiation source and a fiber, not shown here, to generate the illumination spot 39 and the surface.

Due to the wavelength and the angle of incident 66 at the surface as well as the translucent properties of the surface, scattering of the illumination beam 26 takes place. The scattered beam, is the response beam 32 that can be imaged by the image detection component 29.

Figure 5:
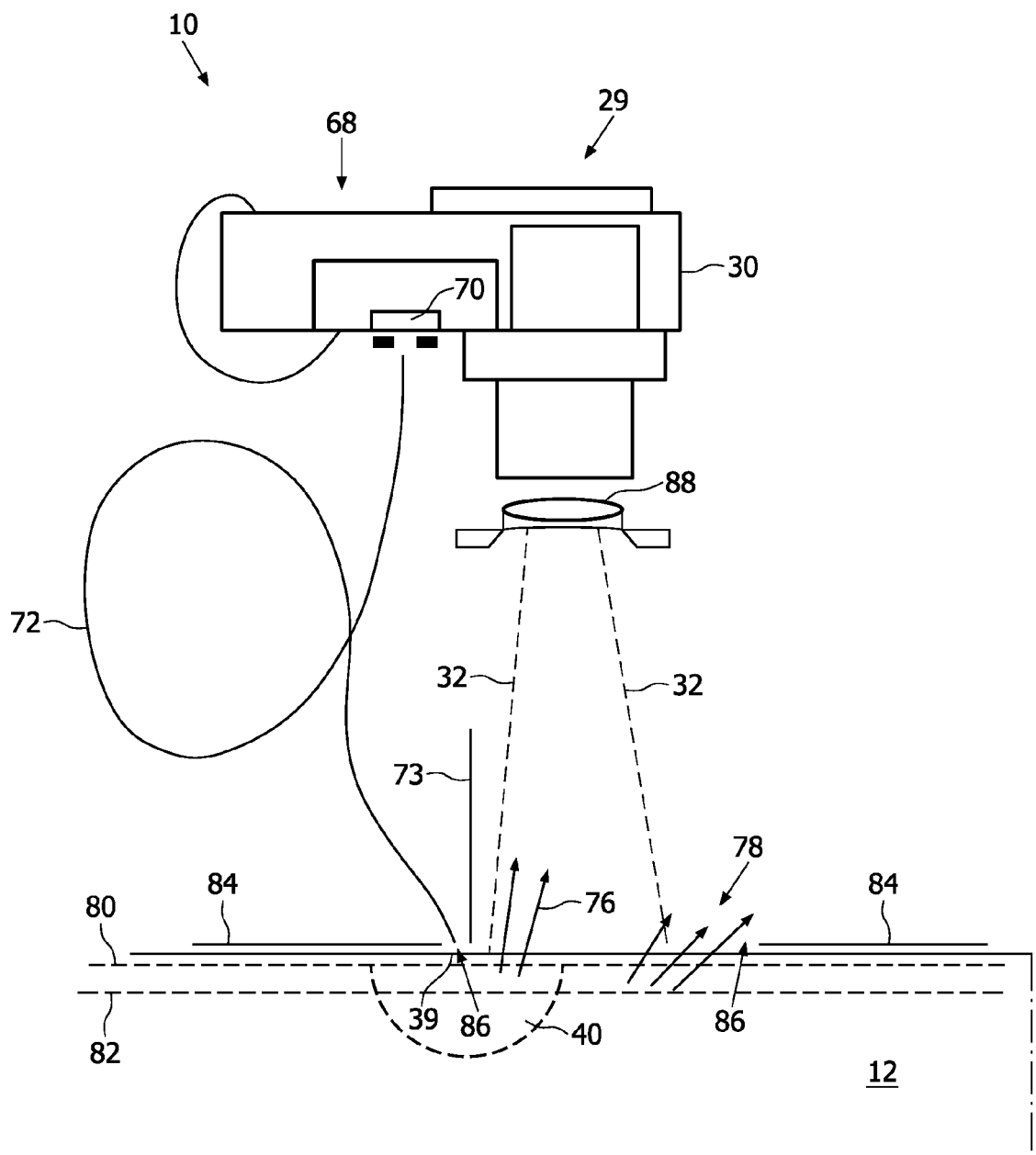
FIG. 5 shows a schematic view of a second embodiment of the present invention.

FIG. 5 shows an embodiment of the invention, performing the optimized imaging of the illumination beam 22, 24, 26 scattered in the sub-surface area 40.

A radiation beam is generated by the Xenon flash of the camera 30 and directed by means of a fiber 72 as an illumination spot 39 onto the surface 14 of the sample 12.

The scattered response beam 66 is imaged by the camera 30, wherein the illumination spot 39 itself is shielded by the mirror means 32.

The irradiation is performed with an illumination device 68, the shielding is performed by a vertical baffle 73. The illumination spot 39 is due to the translucent properties of the material of the sample 12 into the sub-surface areas 40 indicated with the dotted half cycle, indicating the interaction zone. The illumination device 68 comprises a radiation source 70, which is the Xenon flash of the camera 30 and the fiber 72.

The illumination beam scattered directly at the surface is depicted with reference number 76 and the radiation beam, scattered in the sub-surface area 40 is depicted with reference number 78. It can be seen that the deep scattered illumination beam is specially shielded from the scattered beam 76, scattered sub-surface area with a small depth indicated with the line 80 compared to the depth, indicated with the line 82. Both, radiation beam 76 and scattered radiation beams 78 are detected by the detection device 29, which is the camera 30 in particular the digital camera. The position of the camera 30 is chosen such that it is covering an area aside from the illumination spot 39.

A base plate 84 of the optical measurement device 10, wherein the base plate 84 is in close contact with the surface 14 as depicted in FIG. 5, comprises an elongated aperture 86 which is the opening in the base plate 84 shown in the FIG. 5. Due to the fact that the response beam 32, comprising different parts, which are exemplarily shown as part 76 and 78, wherein the different parts are re-emitted from the surface 14 in different locations due to the scattering process forming the response beam 32, the elongated aperture 86 allows the registration of the response beam 32 comprising the different part 76 and at least 78 in the camera 30.

In order to perform a better optical performance of the imaged response beam 32 an optical element 88, in particular a lens 88 is arranged in front of the camera 30.

The response beam 32 is, for better understanding, shown with two depicted lines covering the spatial distribution of the locations the scattered response beam 76 and 78 are re-emitted from the surface 14.

Figure 6:
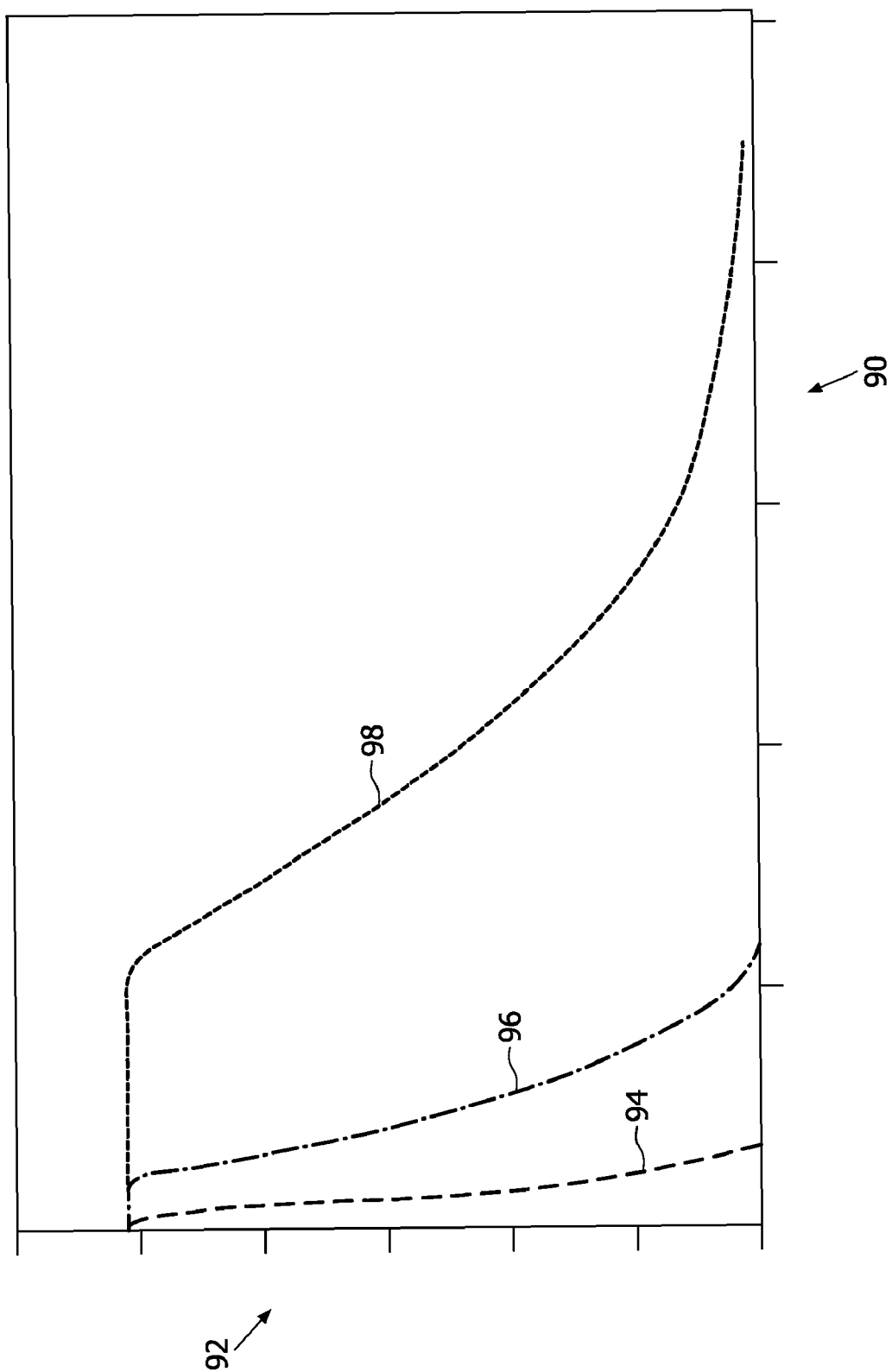
FIG. 6 shows a diagram with information taken from the detected response beam.

FIG. 6 shows the information taken from the image scattering pattern comprising the scattered radiation beams 78 and 76.

In FIG. 6 a diagram showing the extracted information from the detected response beam 32 taken with the camera 30 of the optical measurement device, shown in FIG. 6. Herein the x-axis shows a distance and the y-axis shows an intensity of the detected response beam.

Figure 7:
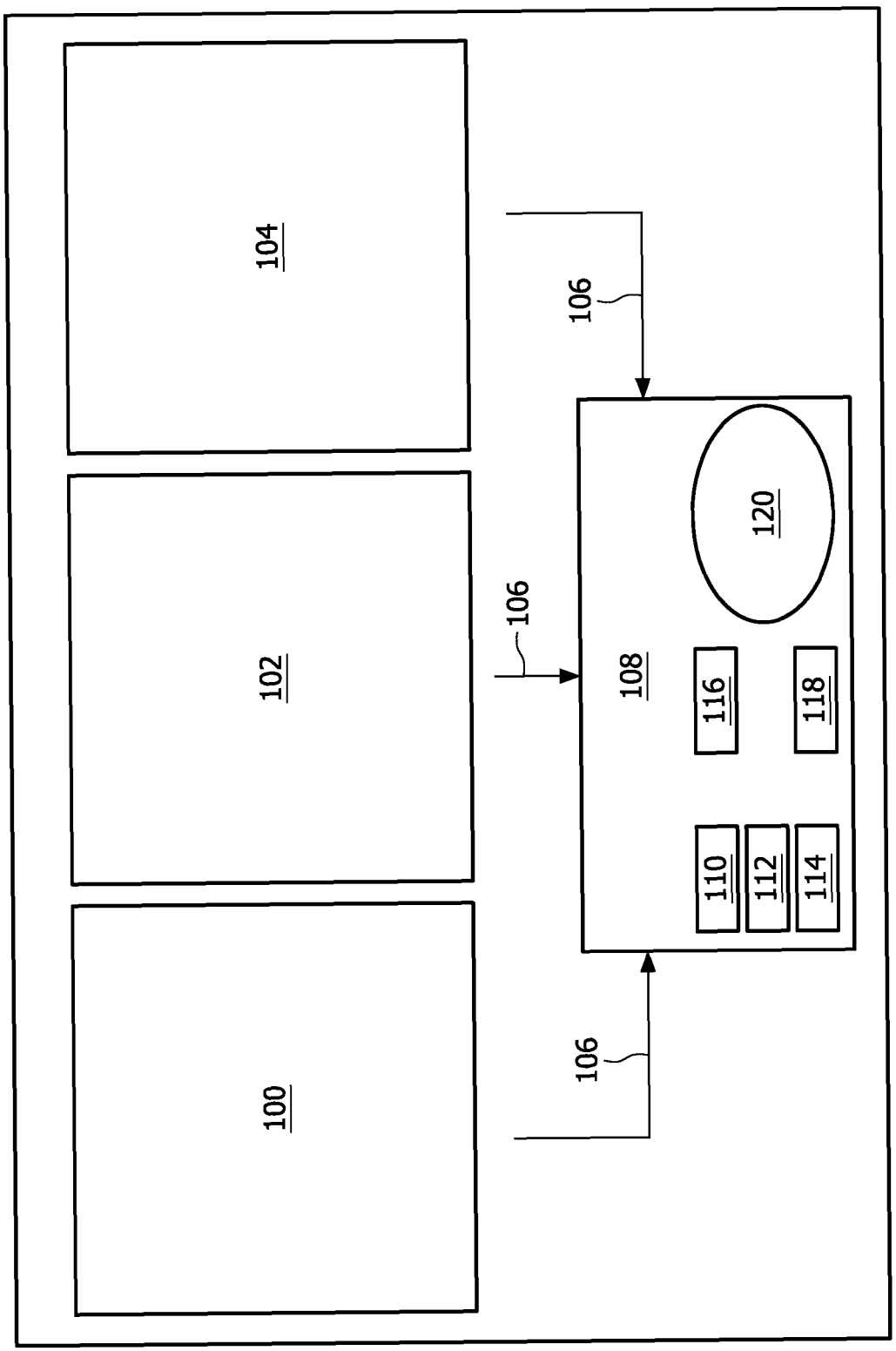
FIG. 7 shows a diagram including a correlation between measurement information and optical appearance.

FIG. 7 shows a skin appearance characterized with light, which is the illumination beam. Herein, the illumination beam is a general wording for the illumination beam 22, 24 and 26 used in the Near field, the Far field and the Deep field investigations.

An area 100 is representing the Near field, photographed with a camera, an area 102 is indicated for the Far field measurement, performed with the Parousiameter, taken with the hemispherical screen and the area 104 is indicated for the measurement of the Deep field. Arrows 106 are indicative for the information, which are comprised in the Near field, the Far field and the Deep field, are taken and given as input to an intelligent computer program, which performs the processing of the Near field, the Far field and the Deep field toward user specific merit factors. The specific outputs are depicted in areas 110, 112, 114 were arrow 110 stands for a scientific user, 112 a professional user and 114 for consumer user. The areas 116 and 118 stand for a more general description of the optical appearance like beauty 116 and medical 118. In the circle 120 a very general description of the human being having the skin, which was investigated, concerning the optical appearance. From 120 a description like health, wellness and feel good can be taken by the user.

With that, to obtain the diagram is a schematic view of the method to be performed from the skin appearance a statement including the information about the skin, the health and the well being of the human being having the human skin. This enables the user of the optical measurement device to investigate the human skin, to obtain different kinds of information derived from the processing of the detected response beam and estimate a correlation factor, called merit factor in order to obtain specific information, useful for the user. User specific means in this context the kind of information, the user like a scientific person, a professional person or just a consumer, is interested in.

Therefore, an objective assessment of the optical appearance of the surface, in particular the human skin is performed with the optical measurement device 10 according to the invention measuring the optical behaviour in three domains: the Near field for visible features, the Far field for reflection features and the Deep field for light scattered in the deeper layer of the skin, called sub-surface areas in here.

These measurements can be done in various spectral bands and polarizations. Measurement combinations like these can be used to monitor certain aspects of the health and the beauty of the skin using special data processing that leads to a limited number of correlation factors.

With that, the invention relates to the method of monitoring the optical appearance of a surface of a sample, in particular a human skin, comprising the steps of illuminating the surface of the skin with at least three illumination means, wherein the illumination beam is incident at different angles at the surface 14. The response beam 32, as a result of the reflection and/or scattering and/or deep scattering behaviour is detected and by data processing a limited number of correlation factors are determined. These correlation factors can be assigned to known features like gloss, number of wrinkles, dark spots, and so on which are known to the user.

With that the method according to the present invention allows a monitoring of the optical appearance of human skin as well as the detection of factors which are important for health like dark spots, indicating for instance mellanome (skin cancer).

The embodiments shown in the foregoing figures are to be understood as examples and not limiting the invention. Essential for any embodiment of the present invention is that the Near Field, the Far Field, the Deep Field, and a spectral in addition are detected.

Therefore, it is obvious that the shown embodiments are only representative for the many possible configurations, depending on their function, of the invention.

The invention claimed is:

1. An optical measurement device for measuring an optical appearance of a surface of a sample (12), in particular the surface (14) of a human skin, wherein the optical measurement device comprises:
a first illumination device (16) for illuminating the surface of the skin (14) with a first illumination beam (22), wherein the first illumination beam (22) is incident at a first angle of incidence (38) onto the surface (14); and
a detection device (28) for detecting a response beam (42), wherein the response beam (42) is a response of the sample (12) to the first illumination beam (22), comprising at least one screen (27) for intercepting the response beam (42) and at least an image detection component (29), characterized in that the optical measurement device (10) comprises a second illumination device (18), wherein the second illumination device (18) is providing a second illumination beam (24) with a second angle of incidence (54) at the surface (14), wherein the first angle of incidence (38) is different from the second angle of incidence,
further characterized in that the screen is a full hemispherical screen, intercepting the response beam in about 360 degrees above the surface of the sample.

2. The optical measurement device of claim 1, characterized in that at least the optical measurement device (10) comprises at least a third illumination device (20), providing a third illumination beam (26) with a third angle of incidence (66) at the surface (12), wherein the third angle of incidence (66) is different from the first (38) and/or the second angle of incidence (54).

3. The optical measurement device of claim 1, characterized in that the image detection component (29) is a camera (30), in particular a digital camera.

4. The optical measurement device of claim 1, characterized in that the screen (27) is a substantially flat screen, covering approximately a quarter hemisphere.

5. The optical measurement device of claim 1, characterized in that the optical measurement device (10) comprises a base plate (84), having a measuring port (86) through which the illumination beam (22, 24, 26) is propagating in order to illuminate the surface (14) and the response beam (42) is propagating towards the detection device (28).

6. The optical measurement device of claim 5, characterized in that the measuring port (86) is designed such that a small area of the surface (14) of the sample (12) is covered, in order to achieve a good spatial resolution.

7. The optical measurement device of claim 5, characterized in that the measuring port (86) has the shape of an elongated aperture in order to detect the response beam (42) that is the response of the sample (12) to the illumination beam (22, 24, 26), scattered at a sub-surface area, wherein the response beam (42) is generated in a distance from the location of the illumination beam (22, 24, 26) incident on the surface (12).

8. The optical measurement device of claim 7, characterized in that the illumination beam directly reflected at the surface (14) is cut off by means of a substantially vertical baffle (73) arranged in the elongated aperture.

9. An optical measurement device for measuring an optical appearance of a surface of a sample, in particular the surface of a human skin, wherein the optical measurement device comprises:
    a first illumination device for illuminating the surface with a first illumination beam, wherein the first illumination beam is incident at a first angle of incidence onto the surface; and
    a detection device for detecting a response beam, wherein the response beam is a response of the sample to the first illumination beam, comprising at least one screen for intercepting the response beam and at least an image detection component;
    a second illumination device, wherein the second illumination device is providing a second illumination beam with a second angle of incidence at the surface, wherein the first angle of incidence is different from the second angle of incidence; and
    a base plate, having a measuring port through which the illumination beam is propagating in order to illuminate the surface and the response beam is propagating towards the detection device, wherein the measuring port has the shape of an elongated aperture in order to detect the response beam that is the response of the sample to the illumination beam, scattered at a sub-surface area, wherein the response beam is generated in a distance from the location of the illumination beam incident on the surface, and wherein the elongated aperture is designed such that the response beam shows a spatial distribution related to a depth at which the illumination beam was scattered in the sub-surface area.

10. The optical measurement device of claim 1, characterized in that the optical measurement device (10) comprises components (32) for shielding the response beam (42) from the illumination beam (22, 24, 26).

11. The optical measurement device of claim 1, characterized in that the optical measurement device (10) comprises at least one mirror (32) for imaging the response beam (42) intercepted by the screen (27) into the image detection component (28).

12. The optical measurement device of claim 2, characterized in that each of the first (16) and/or the second (18) and/or the third illumination device (20) comprises a first and/or a second and/or a third radiation source and/or a first and/or a second and/or a third fiber for directing the first (22) and/or second (24) and/or third illumination beam (26) onto the surface (14) of the sample (12).

13. The optical measurement device of claim 12, characterized in that the optical measurement device (10) comprises one radiation source and a first, a second and a third fiber, wherein the first fiber realizes the first angle of incidence (38), the second fiber realizes the second angle of incidence (54) and the third fiber realizes the third angle of incidence (66) of the respective illumination beam (22, 24, 26).

14. The optical measurement device of claim 12, characterized in that the first fiber and/or the second fiber and/or the third fiber is arrangable in a close distance to the surface (14) in order to realize a small illumination spot (39) at the surface (14).

15. The optical measurement device of claim 1, characterized in that the detection device (28) comprises at least one color filter.

16. The optical measurement device of claim 1, characterized in that the optical measuring device comprises at least one polarisation filter (34, 36).

17. The optical measurement device of claim 1, characterized in that the optical measurement device (10) comprises a calculation device for determining a correlation factor out of the detected response beam.

18. A method for inspecting a surface of a sample and measuring an optical appearance of the sample (12), in particular the surface (14) of a human skin, comprising the following steps:
    illuminating the surface (14) of the sample of the skin (12) with a first illumination beam (22) incident at a first angle of incidence (38) at the surface (14);
    intercepting a response beams (42), wherein the response beam (42) is a response of the sample (12) to at least the first illumination beam, wherein the intercepting is done by a full hemispherical screen in about 360 degrees above the surface of the sample;
    characterized by illuminating the surface (14) with a second illumination beam (24) incident at a second angle of incidence (54) at the surface (14); and
    estimating a first and/or at least a second correlation factor from the intercepted response beam (42);
    assigning the first and/or the at least second correlation factor to a first and/or a second feature of the optical appearance of the sample (12).

19. The method of claim 18, characterized by a second step of illuminating the surface (14) with at least a third illumination beam (26) and estimating at least a third correlation factor in order to obtain at least a third feature of the optical appearance of the sample (12).

20. The method of claim 18, characterized by using a data base in order to perform an assignment of the respective correlation factors to the respective features of the sample (12).

* * * * *